(12) United States Patent
Li et al.

(10) Patent No.: US 8,886,120 B2
(45) Date of Patent: Nov. 11, 2014

(54) LINE-SWITCHABLE NEAR FIELD COMMUNICATION MEDICAL DEVICE

(75) Inventors: Chun-Ying Li, New Taipei (TW);
Yi-Lung Chen, New Taipei (TW);
Shan-Yi Yu, New Taipei (TW); Wen-Yu Tsai, New Taipei (TW)

(73) Assignee: Health & Life Co., Ltd., New Taipei (TW)

( * ) Notice: Subject to any disclaimer, the term of this patent is extended or adjusted under 35 U.S.C. 154(b) by 182 days.

(21) Appl. No.: 13/618,484

(22) Filed: Sep. 14, 2012

(65) Prior Publication Data
US 2014/0017994 A1    Jan. 16, 2014

(30) Foreign Application Priority Data
Jul. 12, 2012    (TW) .............................. 101213432 U

(51) Int. Cl.
*H04B 5/00*    (2006.01)

(52) U.S. Cl.
USPC ........................ 455/41.1; 455/41.2; 600/301

(58) Field of Classification Search
USPC ................ 455/41.1, 39, 67.11, 41.2; 600/301
See application file for complete search history.

(56) References Cited

U.S. PATENT DOCUMENTS

| | | | |
|---|---|---|---|
| 2005/0148828 A1 | 7/2005 | Lindsay | |
| 2011/0082711 A1* | 4/2011 | Poeze et al. | 705/3 |
| 2011/0275907 A1* | 11/2011 | Inciardi et al. | 600/301 |
| 2012/0197090 A1* | 8/2012 | Chen et al. | 600/301 |
| 2012/0329388 A1* | 12/2012 | Royston et al. | 455/41.1 |

* cited by examiner

*Primary Examiner* — Sonny Trinh
(74) *Attorney, Agent, or Firm* — Muncy, Geissler, Olds & Lowe, P.C.

(57) ABSTRACT

A line-switchable Near Field Communication (NFC) medical device comprising: a physiological measurement unit; a Micro Control Unit; a first NFC module in which there are a first memory and a first radio wave antenna communicating with an external second NFC module; a switching module communicating with the Micro Control Unit as well as the first NFC module and enabling or disabling information to be written into or read from the first NFC module's first memory.

16 Claims, 5 Drawing Sheets

LINE-SWITCHABLE NEAR FIELD COMMUNICATION MEDICAL DEVICE

BACKGROUND OF THE INVENTION

1. Field of the Invention

The present invention relates to a medical device, particularly a line-switchable near field communication medical device which depends on a switching module to decide a sequence of information exchange without disturbance.

2. Description of the Related Art

It is necessary for current medical equipment to transfer all kinds of measured physiological information (e.g., body temperature, pulse rate, blood pressure, blood glucose, blood oxygen saturation, EKG, ECG, and respiration parameter) by means of one transmission device which links cable network equipment or wireless network equipment. In virtue of progress of transmission technologies, a Near Field Communication (NFC) system as one contactless short-distance point-to-point communication system of equipment has evolved with a Radio Frequency Identification (RFID) system and interconnection technology integrated. Thus, the NFC medical devices have emerged due to accepted ISO standards on the basis of interface and communication protocols. As shown in FIG. 1, NFC medical equipment based on prior transmission technologies comprises an NFC medical device 90 with a physiological measurement unit 91 for communication, a Micro Control Unit 92 and a first NFC module 93: the Micro Control Unit 92 communicates between the physiological measurement unit 91 and the first NFC module 93 to activate and control measurement of various physiological information in the NFC medical device 90 (e.g., body temperature, pulse rate, blood pressure, blood glucose, blood oxygen saturation, electrocardiogram (EKG or ECG) and respiration parameter); the first NFC module 93 comprises a first memory 931 and a first radio wave antenna 932. On the other hand, an external electronic device 94 used in information exchange with the NFC medical device 90 is provided with a second NFC module 95 which comprises a second memory 951 and a second radio wave antenna 952. As such, the near field (10 cm or so) communication is developed from the external electronic device 94 to the NFC medical device 90.

The NFC medical device 90 based on prior arts to realize near field communication with the external electronic device 94 still has drawbacks as follows: (1) Information exchange is also enabled between the approaching second NFC module 95 and the first radio wave antenna 932 due to an inductive effect when the Micro Control Unit 92 is exchanging information with the first memory 931; (2) Information exchange is also enabled from the Micro Control Unit 92 to the first memory 931 in addition to current exchange between the second NFC module 95 and the first radio wave antenna 932. It can be seen that the NFC medical device based on prior arts is regarded as an unideal design under these conditions inducing disturbance of information exchange or information wrongly understood or accepted. Against this background, how to settle these problems of the prior NFC medical device 90 such as wrong information exchange and realize smooth correct information transfer has become one issue deserving to be overcome by the persons skilled in the art.

Accordingly, the inventor having considered shortcomings of prior NFC medical devices such as application drawback and unideal communication design has studied and developed one solution for smooth, correct and controllable information exchange realized in a line-switchable NFC medical device which can serves the general public and promotes development of the industry.

SUMMARY OF THE INVENTION

The present invention is intended for providing a line-switchable Near Field Communication (NFC) medical device which features controllability of information exchange between the NFC medical device and an external electronic device for realizing correct communication and information exchange without disturbance.

To reach the abovementioned purposes, the present invention employs and comprises the following technical measures: a medical device further comprising a physiological measurement unit to catch a person's at least one physiological parameter; a Micro Control Unit running to activate measurement operations of the physiological measurement unit and communicating with the physiological measurement unit; a first NFC module comprising a first memory and a first radio wave antenna which communicates with an external electronic device's second NFC module; a switching module communicating with the Micro Control Unit and the first NFC module and enabling or disabling information to be written into or read from the first NFC module's first memory.

For technical features and effects in terms of the present disclosure completely understood and recognized, the preferred embodiments and detailed drawings are described hereinafter.

DETAILED DESCRIPTION OF THE PREFERRED EMBODIMENTS

Referring to FIG. 2 which illustrates the present invention of a line-switchable Near Field Communication (NFC) medical device comprises a medical device 10 as a physiological information detector consisting of electronic medical devices for pulse rate, blood pressure, blood glucose, blood oxygen saturation, EKG, ECG, and respiration parameter. The medical device 10 further comprises a physiological measurement unit 11, a Micro Control Unit (MCU) 12, a switching module 13 and a first Near Field Communication (NFC) module 14: (a) the physiological measurement unit 11 is able to catch at least a physiological parameter from one person such as body temperature, pulse rate, blood pressure, blood glucose, blood oxygen saturation, electrocardiogram (EKG or ECG) and respiration parameter; (b) the MCU 12 communicates with the physiological measurement unit 11 and runs for physiological measurements of the medical device 10; (c) the switching module 13 communicating with and installed between the MCU 12 and the first NFC module 14 is used in switching electrical signals and includes, without limitation, relays, reed switches, circuit switches (transistor switches), IC (integrated circuit) switches or others; (d) the first NFC module 14 is either a Near Field Communication (NFC) reader/writer or a Near Field Communication (NFC) tag and further comprises a first memory 141 and a first radio wave antenna 142 communicating each other: (d.1) the first memory 141 is an Electrically Erasable Programmable Read-Only Memory (EEPROM) for storage of numerous information comprising individual information (e.g., name, ID number, height, weight, physiological data etc.), date and time information and replies on the first radio wave antenna 142 to exchange information with an external electronic device 30 (e.g., a portable device or a NFC reader/writer module or a NFC tag module) via radio waves; (d.2) the first radio wave antenna 142 emits radio waves with a frequency of 13.56

MHz. The switching module 13 is used in enabling or disabling information to be written into or read from the first memory 141 of the first NFC module 14. The external electronic device 30 is provided with a second NFC module 31 which is a NFC reader/writer or a NFC tag comprising a second memory 311 and a second radio wave antenna 312. The external electronic device 30 is used in near field (about within 10 cm) communication with the NFC medical device 10 for the purpose of information exchange.

The second memory 311 exchanges information with the medical device 10 (the first radio wave antenna 142) through radio waves from the second radio wave antenna 312 and stores information comprising individual information (e.g., name, ID number, height, weight, physiological data etc.), date and time information. The second radio wave antenna 312 emits radio waves with a frequency of 13.56 MHz. In one embodiment, the external electronic device 30 can be either a smart mobile phone, i.e., a smart mobile phone with an NFC tag integrated, or a tablet or notebook computer, i.e., a tablet or notebook computer with an NFC tag integrated. In addition, the external electronic device 30 can be shaped to a round coin or a piece of paper and regarded as an NFC tag; or the external electronic device 30 can be a contactless smart card, i.e., a contactless smart card such as an Easy Card, an Octopus Card, an E-Wallet or a credit card with an NFC tag integrated. As such, the external electronic device 30 comprising the second NFC module 31 is able to construct an external NFC module corresponding to the medical device 10; the first NFC module and the second NFC module are separately a NFC reader/writer or a NFC tag communicating each other.

Referring to FIG. 3 which illustrates the switching module 13 in the present invention further comprises a first control switch 131 and a second control switch 132: the first control switch 131 communicates with both the MCU 12 and the first memory 141 of the first NFC module 14 and enables or disables the MCU 12 to write information into the first memory 141 or read information from the first memory 141; the second control switch 132 communicates with the first control switch 131, the first radio wave antenna 142 of the first NFC module 14, and the first memory 141 to enable or disable information exchange between the first radio wave antenna 142 and the first memory 141. In other words, the second control switch 132 is used to control (enable or disable) information exchange between the first memory 141 and the second NFC module 31 of the external electronic device 30. Both the first control switch 131 and the second control switch 132 (the switching module 13) includes, without limitation, relays, reed switches, circuit switches (transistor switches), IC (integrated circuit) switches or others, for instance, switches controlled by voltage signals including electric potential change (voltage/potential increase), electric signal change, voltage change, or current change.

Referring to FIGS. 2 and 4 which illustrate controllable operations in the present invention of a line-switchable NFC medical device: (a) S10: Start; (b) S11: Decision of conditions including (b.1) Condition 1: Information is exchanged between the physiological measurement unit 11 (which has been activated) and the first memory 141; (b.2) Condition 2: Information is exchanged between the external electronic device 30 and the first memory 141 of the medical device 10;

(c) S13 (in the case of Condition 1): The switching module 13 disconnects communication between the medical device's first radio wave antenna 142 and the external electronic device 30 when information exchange from the physiological measurement unit 11 to the first memory 141, and recovers the communication between the medical device's first radio wave antenna 142 and the external electronic device 30 when the information exchange completed; (d) S12 (in the case of Condition 2): The switching module 13 disconnects communication between the physiological measurement unit 11 and the medical device's first memory 141 when the second NFC module 31 approaching and communicating with the first NFC module 14, and the second NFC module 31 execute information exchange with the first memory 141 via the second radio wave antenna 312, and the switching module 13 recovers the communication between the physiological measurement unit 11 and the medical device's first memory 141 when the information exchange completed.

Referring to FIGS. 3 and 5 which illustrate alternative controllable operations in the present invention of a line-switchable NFC medical device: (a) S10: Start; (b) S11A: Decision of conditions including (b.1) Condition 1: Voltage of a connection line from the switching module 13 to the MCU 12 increases during information exchange between the physiological measurement unit 11 (which has been activated) and the first memory 141; (b.2) Condition 2: Voltage of a connection line from the switching module 13 to the first radio wave antenna 142 increases when the second radio wave antenna 312 approaching and communicating with the first radio wave antenna 142 of the medical device 10;

(c) S13A (in the case of Condition 1): When information exchange between the physiological measurement unit 11 and the first memory 141, increased voltage on the connection line from the first control switch 131 of the switching module 13 to the MCU 12 is detected and communication between the first radio wave antenna 142 of the medical device 10 and the external electronic device 30 is disconnected by the second control switch 132 of the switching module 13. In contrast to the above example, other changes of electric signals including electric potential change (voltage/potential increase), electric signal change, voltage change, or current change can be used in deciding information exchange between the MCU 12 and the first memory 141 of the medical device 10;

(d) S12A (in the case of Condition 2): When the second NFC module 31 approaching and communicating with the first NFC module 14 for information exchange between the second radio wave antenna 312 and the first radio wave antenna 142, increased voltage on the connection line from the second control switch 132 of the switching module 13 to the first radio wave antenna 142 is detected because a magnetic field induced by the external electronic device 30 approaching the medical device 10 is detected by the first radio wave antenna 142 of the first NFC module 14. As such, information exchange from the external electronic device 30 to the medical device 10 can be determined; communication between the physiological measurement unit 11 and the first memory 141 of the medical device 10 can be disconnected by the first control switch 131 of the switching module 13.

In contrast to the above example, other changes of electric signals including electric potential change (voltage/potential increase), electric signal change, voltage change, or current change can be used in deciding if the external electronic device 30 approaches the medical device 10. As a result, the present invention of a line-switchable NFC medical device features controllability of information exchange in the NFC medical device and realizes ordered, smooth and correct communication and information exchange without disturbance.

It can be seen from the above descriptions that the present invention significantly meets patentability and is applied for the patent. However, the above descriptions present preferred embodiments only which do not limit the scope of the present invention; any equivalent change or improvement based on shapes, structures, features and spirit mentioned in the present invention should be incorporated in claims.

Figure 1:
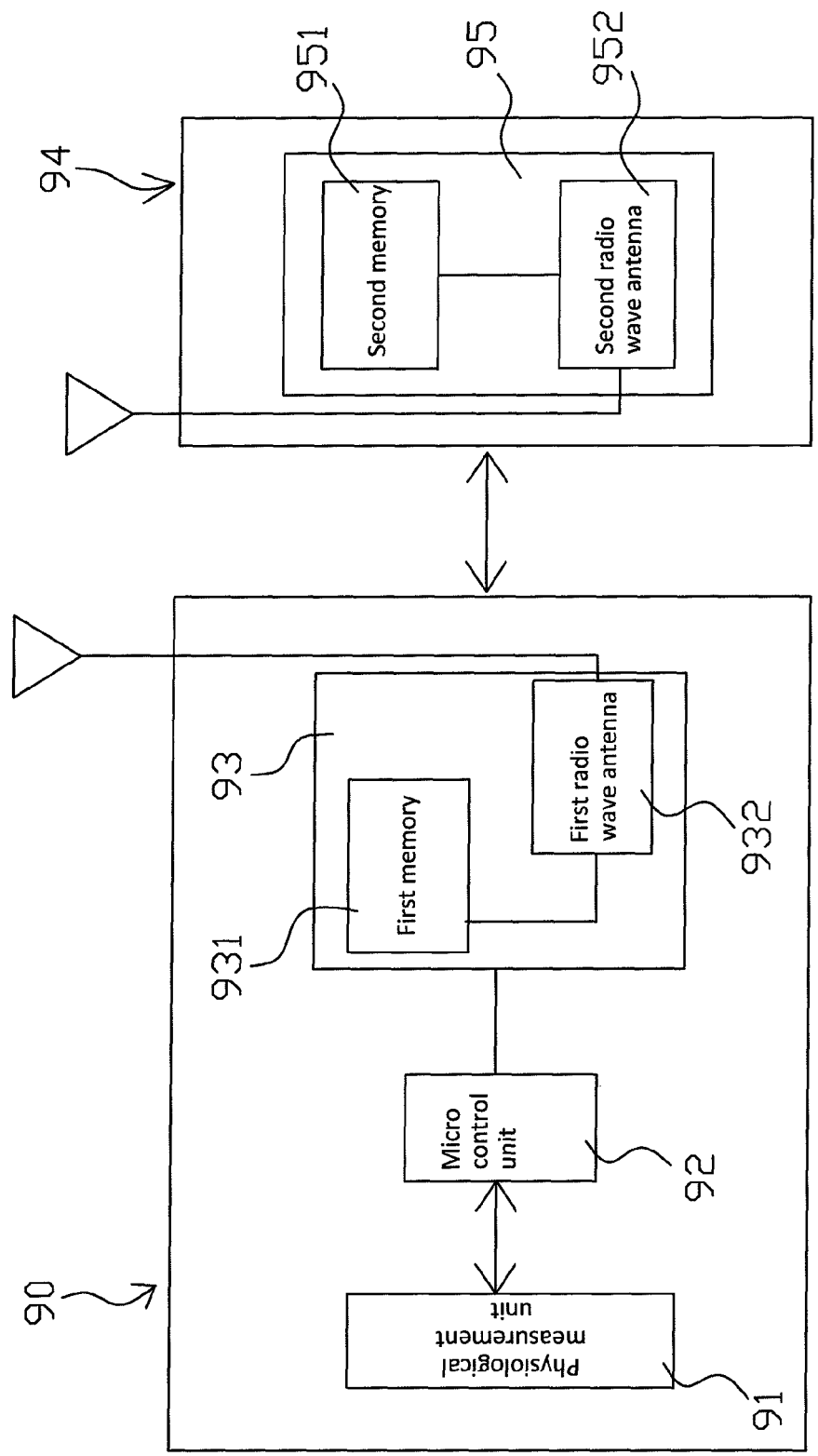
FIG. 1 is a schematic illustration for communication architecture of the NFC medical device based on prior arts.
Figure 2:
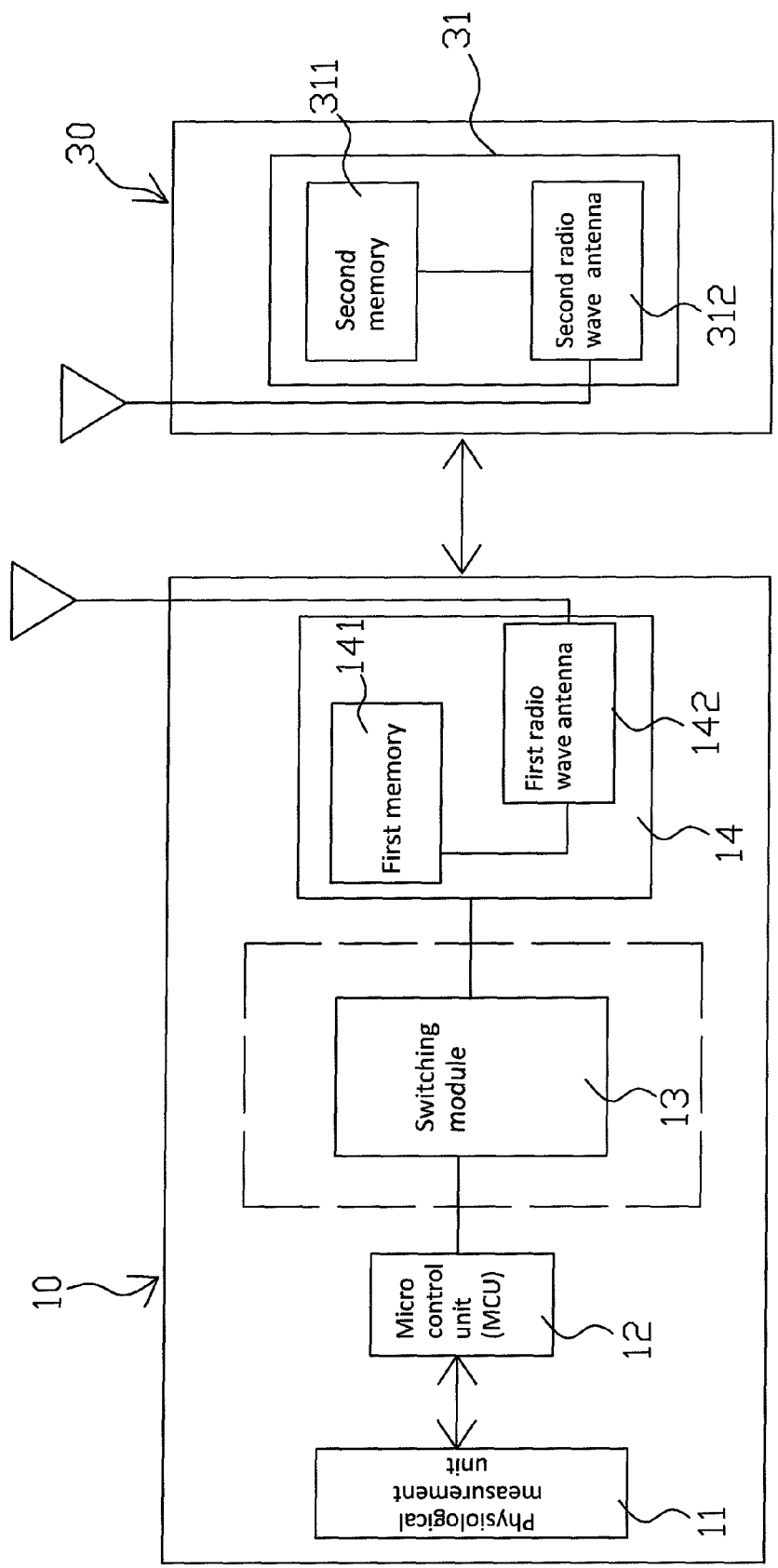
FIG. 2 is a schematic illustration for architecture of the present invention.
Figure 3:
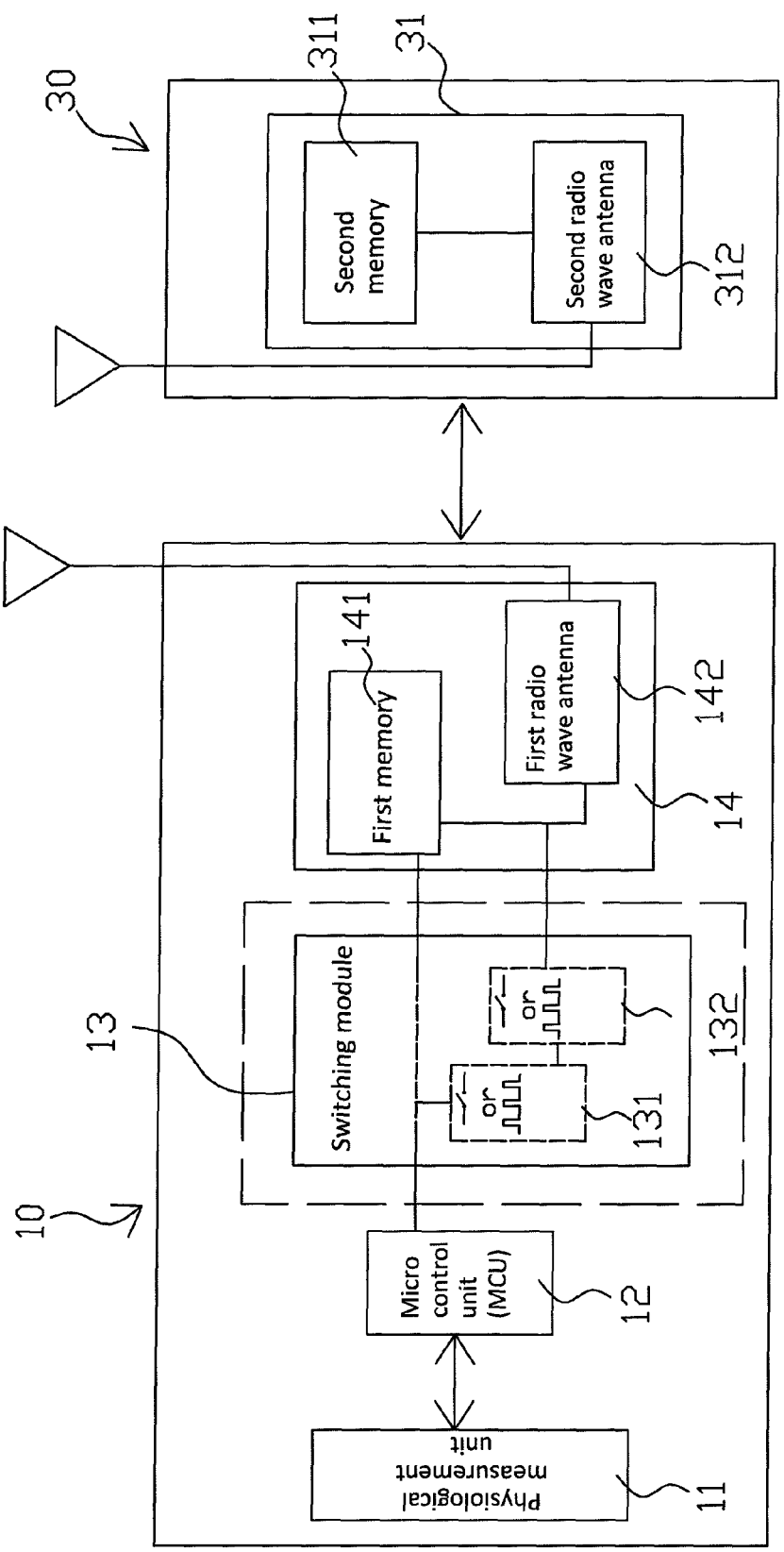
FIG. 3 is an alternative schematic illustration for architecture of the present invention.
Figure 4:
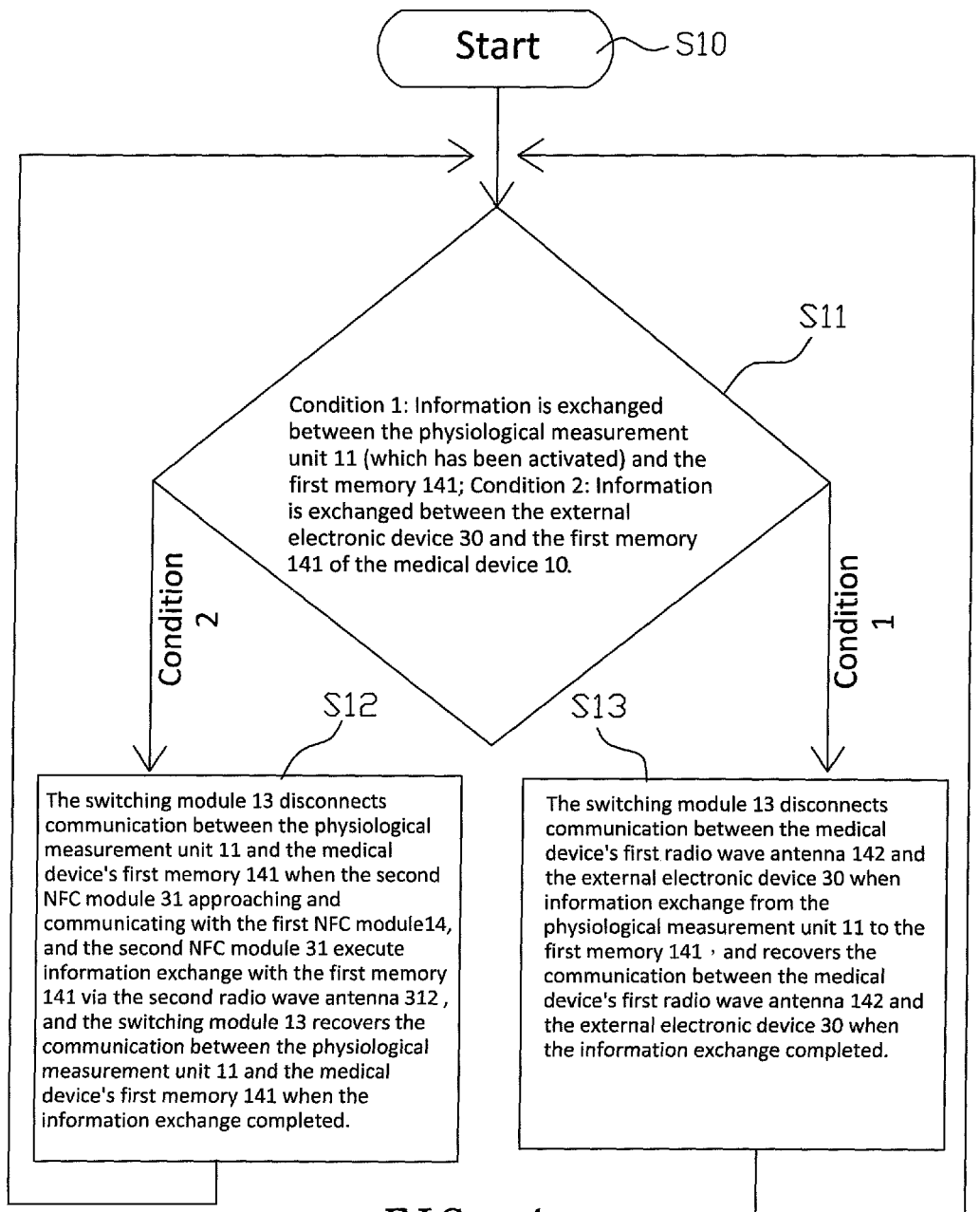
FIG. 4 is a flowchart indicating controllable operations of the present invention.
Figure 5:
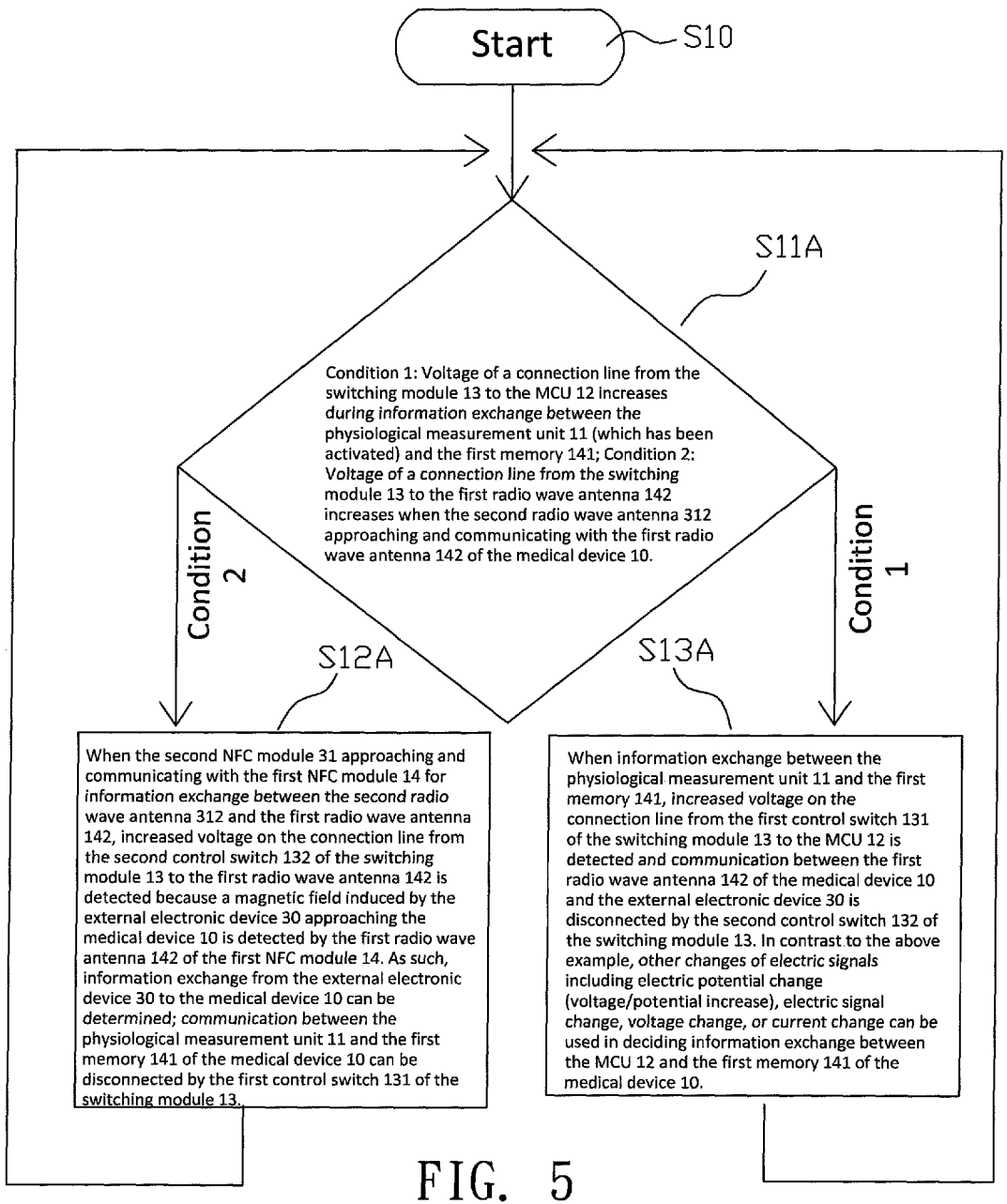
FIG. 5 is an alternative flowchart indicating controllable operations of the present invention.

What is claimed is:

1. A line-switchable Near Field Communication (NFC) medical device for linking an external electronic device, comprising:
    a physiological measurement unit catching a person's at least one physiological parameter;
    a Micro Control Unit (MCU) communicating with said physiological measurement unit and running to activate measurement operations of said physiological measurement unit;
    a first NFC module comprising a first memory and a first radio wave antenna wherein said first radio wave antenna is used to communicate with said external electronic device;
    a switching module communicating with said MCU and said first NFC module and enabling or disabling information to be written into or read from said first NFC module's first memory;
    said switching module disconnects communication between said medical device's first radio wave antenna and said external electronic device during information exchange from said physiological measurement unit to said first memory, and recovers said communication between said medical device's first radio wave antenna and said external electronic device when information exchange completed.

2. The line-switchable NFC medical device according to claim 1, wherein said external electronic device is provided with a second NFC module in which there is a second memory and a second radio wave antenna.

3. The line-switchable NFC medical device according to claim 2, wherein said switching module further comprises a first control switch communicating with said MCU and said first memory and enabling or disabling said MCU to write information into said first memory or read information from said first memory.

4. The line-switchable NFC medical device according to claim 3, wherein said switching module further comprises a second control switch communicating with said first radio wave antenna and said first memory, and enabling or disabling said information exchange between said first radio wave antenna and said first memory.

5. The line-switchable NFC medical device according to claim 4, wherein said second control switch controls information exchange between said first memory and said second NFC module of said external electronic device.

6. The line-switchable NFC medical device according to claim 2, wherein said switching module disconnects communication between said physiological measurement unit and said medical device's first memory when said second NFC module approaching and communicating with said first NFC module, and said second NFC module executes information exchange with said first memory via said second radio wave antenna, and said switching module recovers said communication between said physiological measurement unit and said medical device's first memory when information exchange completed.

7. The line-switchable NFC medical device according to claim 2, wherein said external electronic device is a smart mobile phone, a tablet computer, a notebook computer or a smart card.

8. The line-switchable NFC medical device according to claim 7, wherein said smart card is an Easy Card, an Octopus Card, an E-Wallet or a credit card.

9. The line-switchable NFC medical device according to claim 2, wherein said first NFC module and said second NFC module are separately a NFC reader/writer or a NFC tag communicating each other.

10. The line-switchable NFC medical device according to claim 1, wherein said physiological parameters comprise body temperature, pulse rate, blood pressure, blood glucose, blood oxygen saturation, EKG, ECG, and respiration parameter.

11. The line-switchable NFC medical device according to claim 1, wherein said switching module is a circuit switch, a transistor switch or an IC switch.

12. The line-switchable NFC medical device according to claim 1, wherein said switching module is a relay.

13. The line-switchable NFC medical device according to claim 1, wherein said switching module is a reed switch.

14. The line-switchable NFC medical device according to claim 1, wherein said switching module is a switch controlled by voltage signals.

15. The line-switchable NFC medical device according to claim 14, wherein said voltage signal control comprises electric potential change, voltage/potential increase, electric signal change, voltage change, or current change.

16. The line-switchable NFC medical device according to claim 1, wherein said first memory is an Electrically Erasable Programmable Read-Only Memory (EEPROM).

* * * * *